(12) United States Patent
Peppi et al.

(10) Patent No.: US 11,439,749 B2
(45) Date of Patent: Sep. 13, 2022

(54) APPARATUS AND METHOD FOR TRANS-ROUND WINDOW MEMBRANE DRUG DELIVERY

(71) Applicant: The Charles Stark Draper Laboratory, Inc., Cambridge, MA (US)

(72) Inventors: Marcello Peppi, Cambridge, MA (US); Vishal Tandon, Newton, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 403 days.

(21) Appl. No.: 16/169,498

(22) Filed: Oct. 24, 2018

(65) Prior Publication Data
US 2019/0117884 A1    Apr. 25, 2019

Related U.S. Application Data

(60) Provisional application No. 62/576,852, filed on Oct. 25, 2017.

(51) Int. Cl.
| | | |
|---|---|---|
| *A61M 5/158* | (2006.01) | |
| *A61M 5/142* | (2006.01) | |
| *A61M 5/145* | (2006.01) | |
| *A61F 11/00* | (2022.01) | |
| *A61M 1/00* | (2006.01) | |

(52) U.S. Cl.
CPC .......... *A61M 5/158* (2013.01); *A61F 11/00* (2013.01); *A61M 1/85* (2021.05); *A61M 5/145* (2013.01); *A61M 5/14276* (2013.01); *A61M 2005/1586* (2013.01); *A61M 2210/0662* (2013.01)

(58) Field of Classification Search
CPC .. A61M 5/158; A61M 5/14276; A61M 5/145; A61M 2005/1586; A61M 2210/0662; A61M 1/0084; A61F 11/00
See application file for complete search history.

(56) References Cited

U.S. PATENT DOCUMENTS

| | | | |
|---|---|---|---|
| 6,309,410 B1 | 10/2001 | Kuzma et al. | |
| 2007/0282358 A1* | 12/2007 | Remiszewski | A61B 1/0052 606/159 |
| 2008/0306590 A1* | 12/2008 | Hamilton | A61L 27/50 623/8 |

(Continued)

OTHER PUBLICATIONS

International Preliminary Report on Patentability on PCT PCT/US2018/057322 dated May 7, 2020.

(Continued)

*Primary Examiner* — Dung T Ulsh
(74) *Attorney, Agent, or Firm* — Foley & Lardner LLP

(57) ABSTRACT

The present solution provides trans-round window membrane (RWM) drug delivery. As an overview, the system can include a micropump that is connected to a flexible cannula. The cannula can include a stiffened and sharpened tip to facilitate insertion through the RWM. The cannula can be inserted through the RWM to improve the distribution of the delivered drug throughout the inner ear. The present solution can function as a small implantable or wearable device that can be used for both chronic and acute trans-RWM drug delivery. With this configuration, the micropump can constantly or intermittently deliver, over a period of days to months, small volumes of drugs from an internal reservoir.

14 Claims, 6 Drawing Sheets

(56) References Cited

U.S. PATENT DOCUMENTS

| | | | | |
|---|---|---|---|---|
| 2013/0035662 | A1* | 2/2013 | Decker | A61M 5/329 |
| | | | | 604/500 |
| 2013/0331779 | A1* | 12/2013 | Dhanasingh | A61N 1/0541 |
| | | | | 604/93.01 |
| 2014/0018736 | A1* | 1/2014 | Hessler | A61N 1/0541 |
| | | | | 604/151 |
| 2015/0265824 | A1 | 9/2015 | Lalwani et al. | |
| 2015/0374964 | A1* | 12/2015 | Verhoeven | A61M 5/16804 |
| | | | | 604/247 |

OTHER PUBLICATIONS

International Search Report and Written Opinion on PCT/US2018/057322 dated Feb. 12, 2019.

Tandon et al. "Microfabricated infuse-withdraw micropump component for an integrated inner-ear drug-delivery platform", Biomed Microdevices (2015), 16 pages.

Tandon et al. "Microfabricated Reciprocating Micropump for Intracochlear Drug Delivery with Integrated Drug/Fluid Storage and Electronically Controlled Dosing", HHS Public Access, Author Manuscript, Mar. 7, 2017 (38 pages).

\* cited by examiner

APPARATUS AND METHOD FOR TRANS-ROUND WINDOW MEMBRANE DRUG DELIVERY

CROSS-REFERENCE TO RELATED APPLICATIONS

The present application claims the benefit, under 35 U.S.C. § 119(e), of the filing of U.S. Provisional Patent Application 62/576,852, filed Oct. 25, 2017. This provisional application is incorporated herein by reference for all purposes.

BACKGROUND OF THE DISCLOSURE

Advances in pharmacological technology have provided a number of compounds for the treatment of sudden noise and age-related hearing loss. While these new compounds show promising results, many of them have failed to be effective when delivered systemically due to the blood-cochlear barrier, and local delivery by deposition onto the round window membrane (RWM) is often ineffective because penetration of the compounds through the RWM can be low. The low penetration of the compounds can result in the delivery of compound concentration levels below the therapeutic threshold.

SUMMARY OF THE DISCLOSURE

The present disclosure describes systems and methods that can provide a robust procedure for the effective, local delivery of medications (or more generally, compounds) to the inner ear. The systems and methods can deliver the compounds to the inner ear via a trans-round window membrane (trans-RWM) approach using a catheter inserted through the RWM and connected to an implanted micropump. The micropump can deliver compounds acutely or chronically. The micropump can control the amount of compound delivered directly into the perilymphatic fluid of the scala tympani. The systems and methods can overcome many difficulties that arise from intra-tympanic injections, such as low quantity of drugs crossing the RWM, uneven distribution of drug across the inner ear, and poor drug bioavailability within the cochlea. The systems and methods can be applied both to pharmacokinetics studies, in vivo drug discovery, and the treatment of inner ear diseases in humans. Trans-RWM drug delivery is compatible with numerous drug types, including small molecule and large complex molecules such as proteins, viruses, and liposomes.

According to at least one aspect of the disclosure, a method to deliver a fluid to the inner ear can include implanting a micropump beneath the scalp. The micropump can include a drug reservoir storing a drug or other compound, a fluid storage capacitor, a pump, and an outlet. The method can include implanting a cannula into the patient. The cannula can include a first end coupled with the micropump, and a second end can include a stopper configured to enable the cannula tip to be inserted through a round window membrane and into a cochlea of the patient a predetermined distance. The method can include seating the stopper of the cannula into a round window of the patient. The method can include pumping, by the micropump, the drug from the drug reservoir to the cochlea of the patient via the cannula.

In some implementations, the method can include pumping the drug from the drug reservoir to the cochlea. The method can include injecting a predetermined volume of the drug into the cochlea. The method can include withdrawing, by the micropump, the predetermined volume of a fluid from the cochlea after injecting the predetermined volume of the drug into the cochlea. The method can include storing the predetermined volume of the fluid from the cochlea in the fluid storage capacitor.

The cannula tip can include a beveled tip configured to pierce the round window membrane. The method can include securing the cannula in place with a silicone-based glue.

The cannula can include a first portion that can include polyetheretherketone and a second portion that can include polytetrafluoroethylene. The second portion can include the cannula tip. The cannula can have an inner diameter of between about 15 µm and about 150 µm.

According to at least one aspect of the disclosure, a system to deliver a fluid to the inner ear can include a micropump. The micropump can be configured for implantation beneath the scalp of a patient. The micropump can include a drug reservoir configured to store a drug, a fluid storage capacitor, an outlet, and a pump to pump the drug from the drug reservoir through the outlet. The system can include a cannula. The cannula can include a first end coupled with the outlet of the micropump. The cannula can include a second end that can include a stopper configured to seat into a round window and enable the cannula tip to be inserted through a round window membrane and into a cochlea of the patient a predetermined distance.

In some implementations, the pump can be configured to inject a predetermined volume of the drug into the cochlea. The pump can be configured to withdraw the predetermined volume of a fluid from the cochlea after injecting the predetermined volume of the drug into the cochlea. The micropump can be configured to store the predetermined volume of the fluid from the cochlea in the fluid storage capacitor.

The cannula tip can include a beveled tip configured to pierce the round window membrane. The cannula can include a first portion that can include polyetheretherketone and a second portion that can include polytetrafluoroethylene. The second portion can include the cannula tip. The second portion can be between about 2 cm and about 5 cm long.

The stiffness of the second portion can be greater than the stiffness of the first portion. The cannula can have an inner diameter of between about 15 µm and about 150 µm. The cannula tip can include a bevel between about 10 degrees and about 45 degrees.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present solution provides trans-RWM drug delivery. As an overview, the system can include a micropump that is connected to a flexible cannula. The cannula can be inserted through the RWM. The present solution can function as small implantable or wearable device that can be used for both chronic and acute trans-RWM drug delivery. With this configuration, the micropump can constantly or intermittently deliver, over a period of days to months, small volumes of drugs from an internal reservoir. In some implementations, syringe pumps can be used for acute procedures. The micropump can drive fluid flow through a cannula to deliver multiple doses on a pre-programmed schedule. The solution is compatible with delivery of a timed series of several agents.

The present solution can be used in place of (or in conjunction with) systemic drug delivery. Systemic delivery can require higher doses of compounds when compared to the local compound delivery provided by the present solution. The high doses associated with systemic delivery can often produce undesirable side effects that, in some cases, discourage patients from continuing treatment. Moreover, systemically administered drugs often are modified by hepatocytic enzymes once drugs pass the hepatic system, further reducing drug activity and producing a poor therapeutic effect in the inner-ear. By delivering the compounds directly to the inner ear, the present solution can overcome these problems with systemic drug delivery because the compounds are injected directly into cochlear fluids. Direct injection of the compounds into the cochlear fluids enables a smaller dose when compared to systemic delivery.

Figure 1:
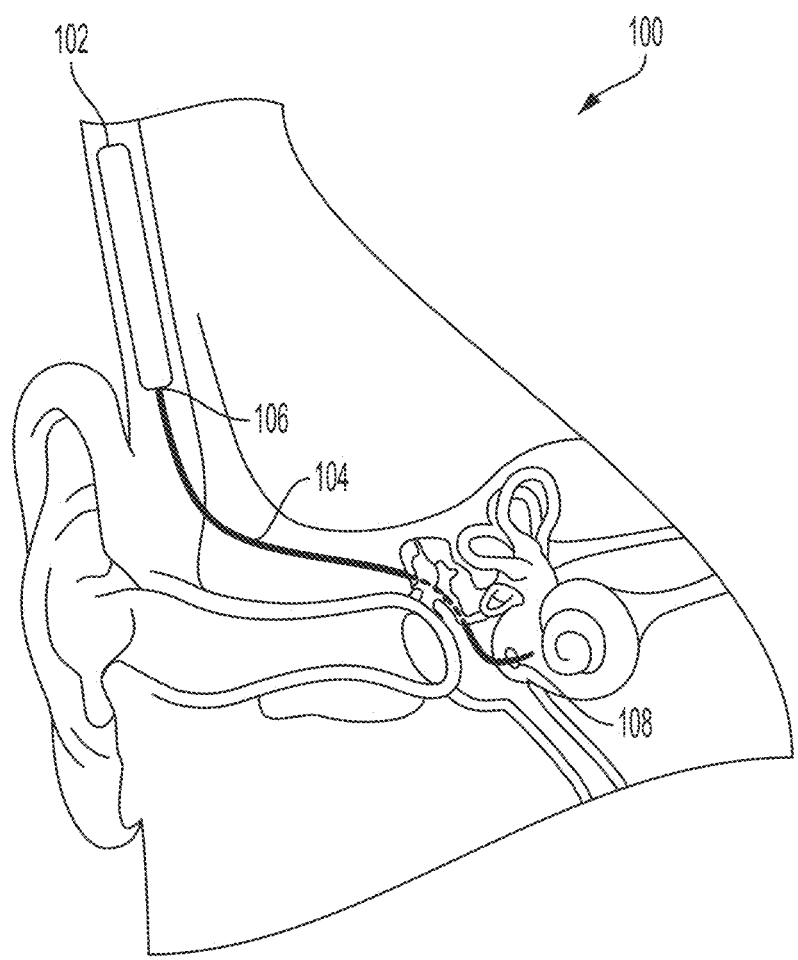
FIG. 1 illustrates an example system to inject compounds into the inner ear.

FIG. 1 illustrates an example system 100 to inject compounds into the inner ear. The system 100 can include a micropump 102. The system 100 can include a cannula 104. The cannula 104 can be coupled with the micropump's pump outlet 106. The cannula 104 can be inserted through the round window membrane 108 and into the inner ear.

Figure 2:
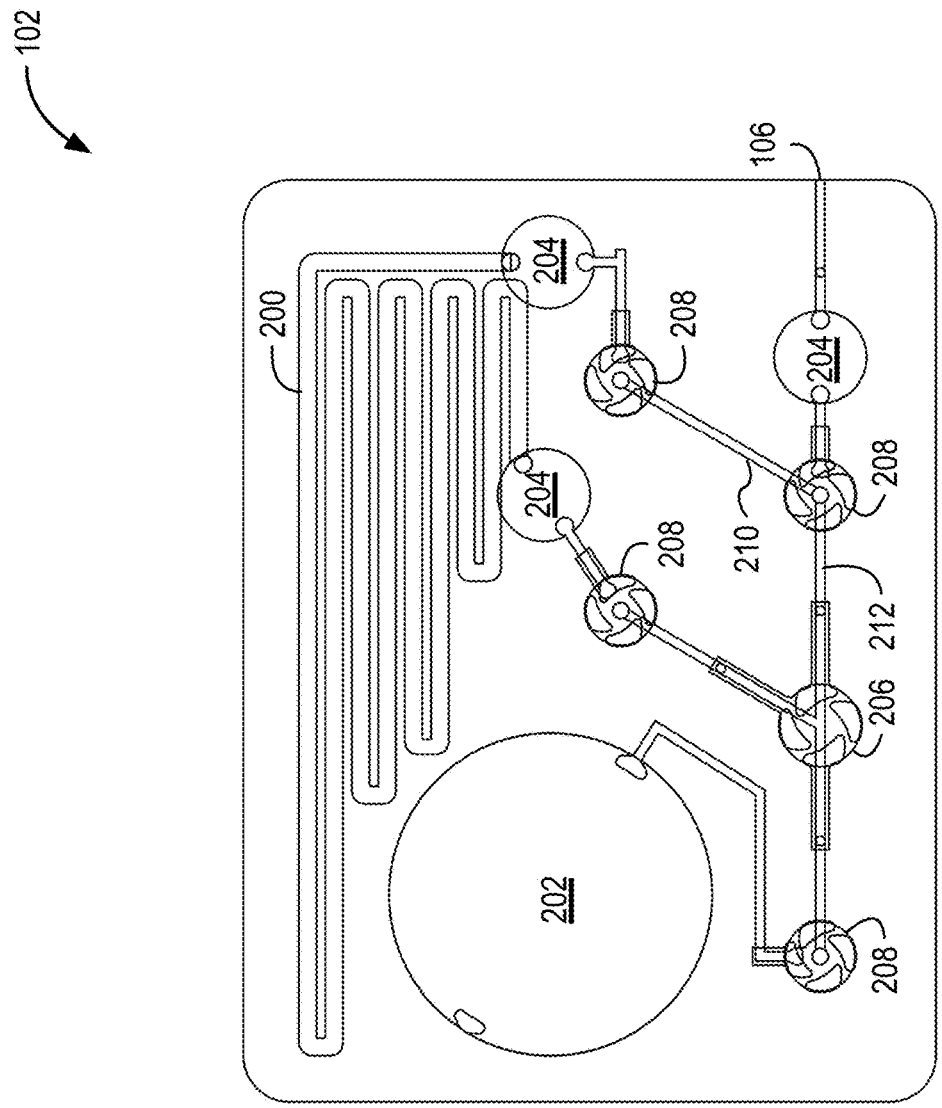
FIG. 2 illustrates a top view of an example micropump for use in the example system illustrated in FIG. 1.

The micropump 102 is described further in relation to FIG. 2, among others. As an overview, the micropump 102 can be a reciprocating, automated fluid injection system. The micropump 102 can include an integrated drug reservoir. The drug stored in the drug reservoir can be referred to as a compound and the drug reservoir can be referred to as a compound reservoir. The micropump 102 can dispense the compound from the compound reservoir to the inner ear, via the cannula 104, at predetermined intervals. The micropump 102 can be configured to both inject the compound into the inner ear and to withdraw fluid from the inner ear so that the net volume added to the inner ear is substantially zero. The micropump 102 can include one or more internal pumps and valves that can control the withdrawal and infusion fluid to and from the micropump. For chronic delivery applications, the micropump 102 can be worn around the head or implanted. For example, as illustrated in FIG. 1, the micropump 102 can be housed in a sealed housing and implanted under the scalp behind or near the ear.

The system 100 also includes the cannula 104. The cannula 104 can include a sharp, smooth tip. For example, the tip of the cannula 104 can include a sharpened bevel. The sharp, smooth tip can enable the cannula 104 to pierce the round window membrane 108. In some implementations, the sharp, smooth tip can enable the cannula 104 to pierce the round window membrane 108 without collapsing the round window membrane 108. The cannula 104 is described further in relation to FIG. 3, among others.

FIG. 2 illustrates a top view of an example micropump 102. The micropump 102 can include a drug reservoir 200 and a fluid storage capacitor 202. A drug-containing fluid can be dispensed from the micropump 102 via the outlet 106. The micropump 102 can include a pump 206. The micropump 102 can include a plurality of valves 208 and fluid capacitors 204.

The micropump 102 can be a multilayered device. The micropump 102 can include fluid routing layers. For example, the fluid routing layers can include the drug reservoir 200, fluid storage capacitor 202, fluid capacitors 204, the channels 210 therebetween, and a loading chamber 212. The micropump 102 can include one or more active layers. The active layers can include the actuators of the valves 208 and the pump 206, the controller that controls the valves 208 and the pump 206, and a power source for powering the micropump 102. The fluid routing layers can be separated from the active layers by a membrane. The fluid routing layers can include polyetherimide (PEI). The membrane separating the fluid routing layer and the active layers can include a flexible membrane, such as polyimide and Viton.

The micropump 102 can include the drug reservoir 200. The drug reservoir 200 can be machined (e.g., laser etched) into one or more of the fluid routing layers. The drug reservoir 200 can be configured as a serpentine or other channel structure. The drug reservoir 200 can be configured as a channel with an inlet and an outlet such that a fluid can be pumped into the inlet to force the drug from the outlet of the drug reservoir 200 and into one of the channels 210. The drug reservoir 200 can have a channel width between about 300 µm and about 1200 µm, between about 400 µm and about 1000 µm, between about 500 µm and about 900 µm, between about 600 µm and about 800 µm, or between about 700 µm and about 800 µm. The drug reservoir 200 can have a channel height between about 300 µm and about 1200 µm, between about 400 µm and about 1000 µm, between about 500 µm and about 900 µm, between about 600 µm and about 800 µm, or between about 700 µm and about 800 µm. The drug reservoir 200 can have a total channel length between about 300 mm and about 100 mm, between about 300 mm and about 800 mm, or between about 300 mm and about 600 mm.

The micropump 102 can include a fluid storage capacitor 202. The fluid storage capacitor 202 can be a cylinder formed in the fluid routing layer. The fluid storage capacitor 202 can have a diameter of between about 10 mm and about 20 mm, between about 12 and about 18 mm, or between about 14 and about 16 mm. The fluid storage capacitor 202 can be configured to store fluid withdrawn from the inner ear of the patient. The fluid storage capacitor 202 can also provide fluid to the inlet of the drug reservoir 200 to force the drug out of the outlet of the drug reservoir 200.

The micropump 102 can also include a plurality of fluid capacitors 204. The fluid capacitors 204 can be machined in line with the fluid channels 210 and loading chamber 212 of the fluid routing layer. The fluid capacitors 204 can have a diameter of between about 2 mm and about 10 mm, between about 2 mm and about 8 mm, between about 2 mm and about 6 mm, or between about 4 mm and about 6 mm. The fluid storage capacitor 202 and the fluid capacitors 204 can have a ceiling formed by the membrane separating the fluid routing layers and the active layers.

The fluid capacitors 204 can improve power efficiency, help to regulate peak flow rates, and provide fluid storage. For example, the channels 210 of the micropump 102 can have relatively high fluid resistances, which can cause a relatively large time constant associated with expelling fluid from the micropump 102. Accordingly, with a relatively large time constant, the valves 208 may need to be powered for several seconds to open the valves and to enable the pump chamber to have time to fully drain or fill. The fluid capacitors 204 that are in line with the fluid channels 210 have lower fluid resistance and can enable relatively fast transfer of fluid into and out of the pump chamber followed by passive fluid flow associated with the pressure equilibration of the fluid capacitors 204. This can reduce the amount of time valves 208 are held open (to on the order of tens of milliseconds) and can reduce power consumption. The fluid capacitors 204, for example the fluid capacitor 204 near the outlet 106, can attenuate flow rate bursts generated by pump strokes and reduce large peak flow rates.

The micropump 102 can include one or more pumps 206. The pump 206 can include an actuator in the active layers of the micropump 102. The actuator can hold electromagnets in place. When the electromagnets are unpowered, springs can keep the actuator heads pressed against the polyimide membrane. Pressure against the polyimide membrane presses the Viton layer against an opening to the cylinder of the valve 208 formed in the fluid layer and forms a fluidic seal that closes the valve of the pump 206.

Cycling the actuator of the pump 206 can result in fluid displacement in the pump's fluid chamber. The valves 208 can be cycled (e.g., opened or closed) to control the direction of the fluid flow through the micropump 102. For example, for each stroke type, one valve can act as an intake valve and another valve can act as an expulsion valve. At the beginning of a pump stroke, the intake valve opens, and then the pump actuator is powered resulting in fluid being drawn into the pump chamber from an adjacent fluidic capacitor. Next, the intake valve closes. Then the expulsion valve opens, followed by deactivation of the pump actuator, resulting in fluid being pushed out of the pump chamber into a different fluidic capacitor. Finally, the expulsion valve closes. Depending on which valves are chosen as the intake and expulsion valves, the pump can produce three different types of pump strokes: infusion (e.g., fluid is pumped out of the micropump 102), withdrawal (e.g., fluid is pumped from an external source into the micropump 102), and drug refresh or priming (e.g., fluid is pumped into the loading chamber 212 to be pumped out of the micropump 102 at the end infusion stroke).

The micropump 102 can include one or more valves 208. The valves 208 can have a construction similar to the pump 206. For example, the valves 208 can include a cylinder chamber formed into the fluidic layers. The valves 208 can include an actuator in the active layers that holds electromagnets in place. When the electromagnets are unpowered, the valves can be held in a closed position by a spring that forces the actuator against the membrane to form a seal in the opening of the cylinder chamber of the valve 208. Activation of the actuator can force the electromagnets against the spring and away from the membrane to enable fluid to flow through the valve 208.

Figure 3:
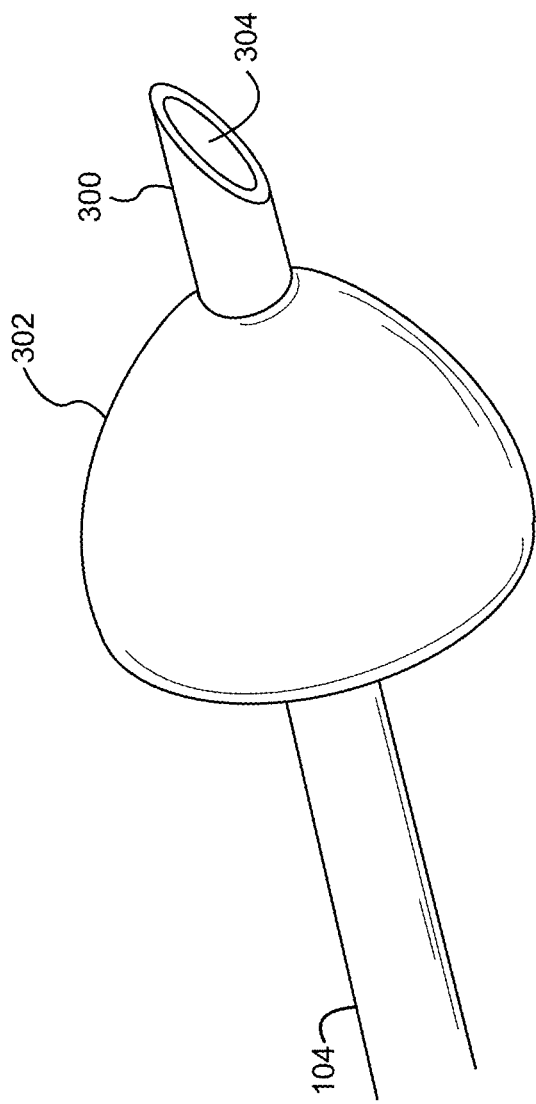
FIG. 3 illustrates an example tip of a cannula that can be used in the example system illustrated in FIG. 1.

FIG. 3 illustrates an example tip 300 of the cannula 104. The cannula 104 can include the tip 300 and a stopper 302. The tip 300 can include an outlet 304 that enables fluid to flow into and out of the tip 300 and cannula 104.

The cannula 104 can include a plurality of different materials. The cannula 104 can include a plurality of different portions and each of the different portions can include a different material. For example, a first portion of the cannula 104 can include polyetheretherketone (PEEK) tubing. The first portion of the cannula 104 can couple with the micropump 102. The first portion of the cannula 104 can be between about 2 cm and about 10 cm, between about 2 cm and about 8 cm, or between about 3 cm and about 6 cm. The first portion of the cannula 104 can have an inner diameter (ID) between about 50 μm and about 300 μm, between about 100 μm and about 200 μm, or between about 150 μm and about 200 μm.

The cannula 104 can include a second portion. The second portion can include the tip 300. The second portion can include Polytetrafluoroethylene (PTFE) tubing. The second portion can be between about 1 cm and about 5 cm, between about 2 cm and about 5 cm, or between about 3 cm and about 5 cm in length. In some implementations, the first and second portion of the cannula 104 can be coupled together by Tygon® tubing.

The tip 300 can have an outer diameter of between 10 μm and 200 μm, between about 10 μm and about 150 μm, or between about 50 μm and about 100 μm. The tip 300 can have an inner diameter between 5 μm and about 200 μm, between about 15 μm and about 150 μm, or between about 50 μm and about 110 μm.

The tip 300 can include a bevel that enables the tip 300 to pierce the round window membrane. The angle of the bevel can be between about 10 degrees and about 45 degrees, between about 15 degrees and about 45 degrees, or between about 25 and about 45 degrees. In some implementations, the bevel is 30 degrees.

The tip 300 can be inserted through the round window membrane 108 such that the catheter's tip bathes in the perilymphatic fluid of the scala tympani. The tip 300 can have a hardness (or stiffness) that is substantially greater than the body of the cannula 104. The stiffened tip 300 can facilitate penetration of the round window membrane 108. In some implementations, the cannula 104 is bent at an angle that substantially matches the middle ear anatomy to facilitate insertion through the round window membrane 108. In some implementations, the bend in the cannula 104 can be near the tip 300.

The tip 300 can penetrate several millimeters into the scala tympani. For example, the tip 300 can penetrate between about 1 mm and about 5 mm or between about 1 mm and about 3 mm into the scala tympani. The tip 300 can include a stopper 302 that can prevent the tip 300 from penetrating too deep into the scala tympani. For example, the stopper 302 can be positioned about 3 mm from the end of the tip 300 such that the tip 300 is positioned 3 mm into the scala tympani when the stopper 302 comes into contact with the round window membrane 108. In some implementations, the stopper 302 can help create a seal between the cannula 104 and the round window membrane 108 to substantially prevent fluid leak from the inner ear.

The tip 300 can be coated with a soft, silicone-like material that seals against the round window membrane 108 following insertion through the round window membrane 108. The cannula 104 can be flexible to facilitate insertion through the round window membrane 108 during surgical procedures. The cannula 104 can be locked within the middle ear space to prevent movement of the cannula 104 after implantation.

The cannula 104 can be coated with a material that releases anti-inflammatory compounds to control middle ear infection. For example, the cannula 104 can be coated with dexamethasone and/or methylprednisolone. In some implementations, the cannula 104 can remain in place for several weeks or months. In other implementations, the cannula 104 can be used acutely and then removed.

Figure 4:
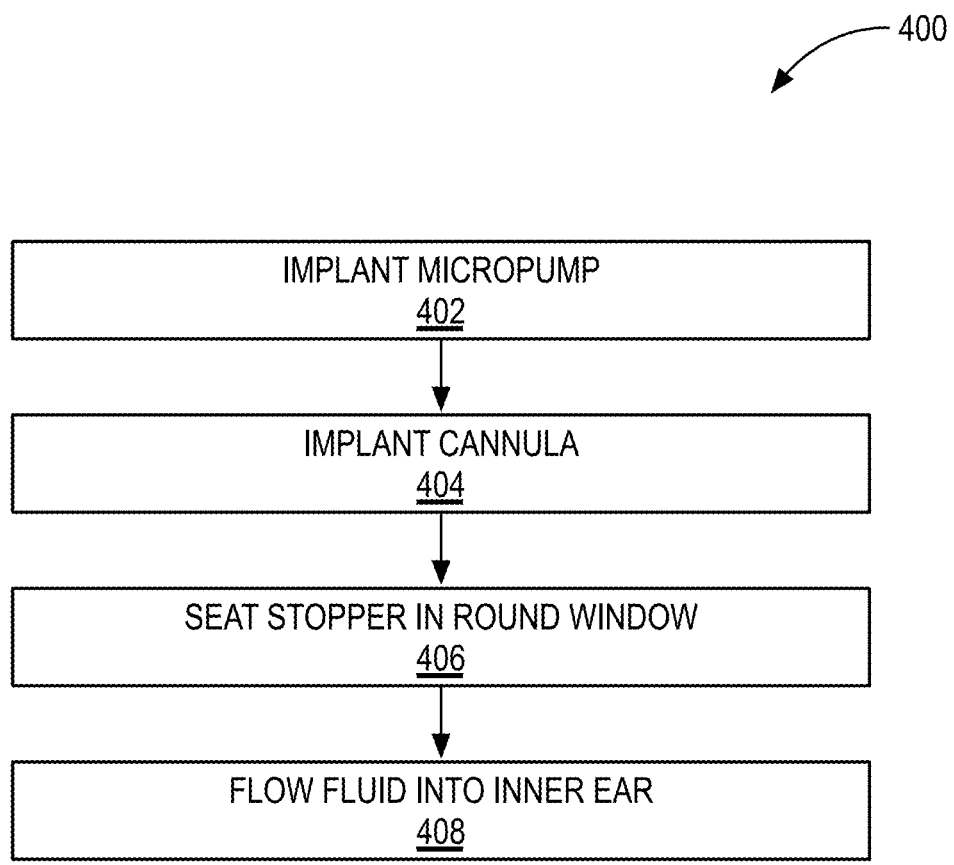
FIG. 4 illustrates a block diagram of an example method to flow fluid into the inner ear of a patient using the example system illustrated in FIG. 1.

FIG. 4 illustrates a block diagram of an example method 400 to flow fluid into the inner ear of a patient. The method 400 can include implanting a micropump (BLOCK 402). The method 400 can include implanting a cannula (BLOCK 404). The method 400 can include seating a stopper in the round window (BLOCK 406). The method 400 can include flowing a fluid into the inner ear (BLOCK 408).

As set forth above, the method 400 can include implanting a micropump into a patient (BLOCK 402). Referring also to FIGS. 1-3, the micropump can be the micropump 102 illustrated in FIGS. 1 and 2. The micropump 102 can include a drug reservoir 200 for the storage of drugs or other fluids to be injected into the inner ear of the patient. The micropump 102 can include a fluid storage capacitor 202. After injecting fluid into the inner ear, the micropump 102 can withdraw fluid from the inner ear and store the fluid in the fluid storage capacitor 202 such that the net fluid displacement from the injections by the micropump 102 is substantially zero for a cycle that includes an injection phase and a withdrawal phase. The micropump 102 can include a pump 206 that can pump fluid from the drug reservoir 200 into the inner ear and that can withdraw fluid from the inner ear for storage in the fluid storage capacitor 202. The micropump 102 can be implanted through an incision in the patient's scalp. The micropump 102 can be implanted between the patient's scalp and skull near the mastoid process and coupled with the skull with surgical screws. In some implementations, the micropump 102 can be implanted in the mastoid cavity. In some implementations, the micropump 102 is not implanted under the patient's scale. For example, the implantation of the micropump 102 can include forming an access port in the patient's scalp that enables the cannula to pass from the micropump 102 outside the scalp to beneath the patient's scalp and toward the inner ear. The micropump 102 can then be worn by the patient in a headband for acute (e.g., short term) drug delivery to the inner ear.

The method 400 can include implanting the cannula (BLOCK 404). The cannula can be implanted into the patient such that a first end of the cannula is coupled with the micropump 102 and a second end (with the cannula's tip) is disposed toward the patient's round window. The micropump 102 and the cannula 104 can be implanted using, for example, retro-auricular, ventral, or trans-tympanic surgery. During the retro-auricular approach, the mastoid process can be opened with a blade and the cochlea and the round window membrane 108 can be exposed. After the cannula 104 is encased in the middle ear between the RWM niche and the mastoid process, the cannula 104 can be inserted through the round window membrane 108 and sealed or glued in place. In the ventral lateral surgery, the ventral bulla can be opened, allowing more direct exposure of the round window membrane 108. In a trans-tympanic surgery, a small incision can be created in the eardrum and a tube is inserted within the tympanic membrane. Then, the cannula 104 can be inserted within the tube in the tympanic membrane tube reaching the RWM.

The method 400 can include seating the stopper in the round window (BLOCK 406). Also referring to FIG. 3, among others, the cannula 104 can include a stopper 302. The stopper 302 can be cone-shaped and can be configured to seat within the round window or the piercing made in the round window membrane made by the tip 300. Seating the stopper 302 in the round window membrane can project the tip 300 into the inner ear a predetermined length. In some implementations, the cannula 104 does not include a stopper 302 and the cannula 104 can be held in place once the tip 300 pierces the round window membrane with a silicone-based glue.

The method 400 can include flowing a fluid into the inner ear (BLOCK 408). Flowing the fluid into the inner ear can include priming the micropump 102, infusing the fluid into the inner ear, and then withdrawing fluid from the inner ear. For example, to prime the micropump 102, a first valve 208 coupled with the first end of the drug reservoir 200 can be opened and the pump 206 can be activated to draw the drug-containing fluid from the drug reservoir 200 into a loading chamber coupled with the outlet 106. Once the first valve 208 is closed, a second valve 208 coupled with the second end of the drug reservoir 200 can be opened to the fluid previously in the loading chamber (and displaced by the drug-containing fluid) into the opposite end of the drug reservoir 200 from which the drug-containing fluid was drawn. To infuse the drug-containing fluid into the inner ear, fluid can be pumped from the fluid storage capacitor 202 toward the outlet 106, which can force the drug-containing fluid in the loading chamber out through the outlet 106. After the drug has been allowed to diffuse for some time in the inner ear, the micropump 102 can withdraw a volume of fluid from the cochlea. The withdrawn volume can be substantially the same volume as the volume of the drug infused into the cochlea. In some implementations, an additional compound or drug can be introduced into the drug reservoir 200 from an external reservoir when the level of compound in the drug reservoir 200 falls below a predetermined level.

The above-described methods can also be used to inject large or lipophobic compounds that may not be suitable for delivery to the inner ear via other methods. For example, other methods may deliver these compounds to the inner ear by placement of these compounds within a liquid or gel formulation. The formulation can then be placed on the RWM. The compound can pass into the cochlea via passive transport through the RWM. This transport mechanism is not effective for large or lipophobic drugs, and such drugs can only pass through the RWM through slow, active transport mechanisms. Also, the pharmacokinetics of trans-RWM delivery are difficult to predict. Additionally, RWM delivery can result in uneven distribution of drug across the inner ear, as well as poor bioavailability of drugs within the cochlea. In order to compensate for the uneven distribution and the low level of drugs within the cochlea, large volumes of drugs are delivered in the middle ear, producing potential local toxicity. The above-described methods of using the system 100 for trans-RWM drug delivery can enable the use of many types of compounds, such as large molecule and lipophobic compounds. The above-described methods provide direct access to the perilymphatic fluid of the cochlea, which can enable more even distribution of the compounds within the inner ear.

Figure 5:
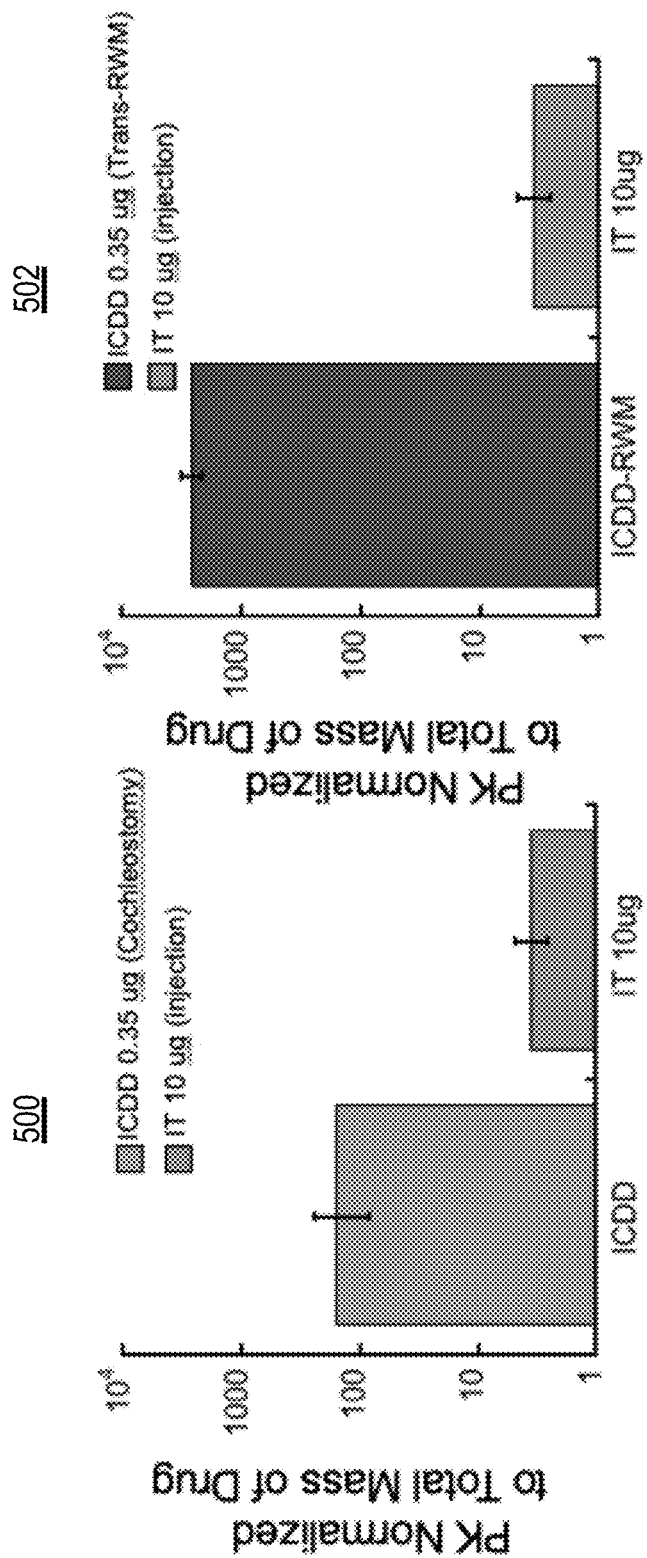
FIGS. 5 and 6 illustrate plots of pharmacokinetics (PK) and pharmacodynamics (PD) across different delivery methods.
Figure 6:
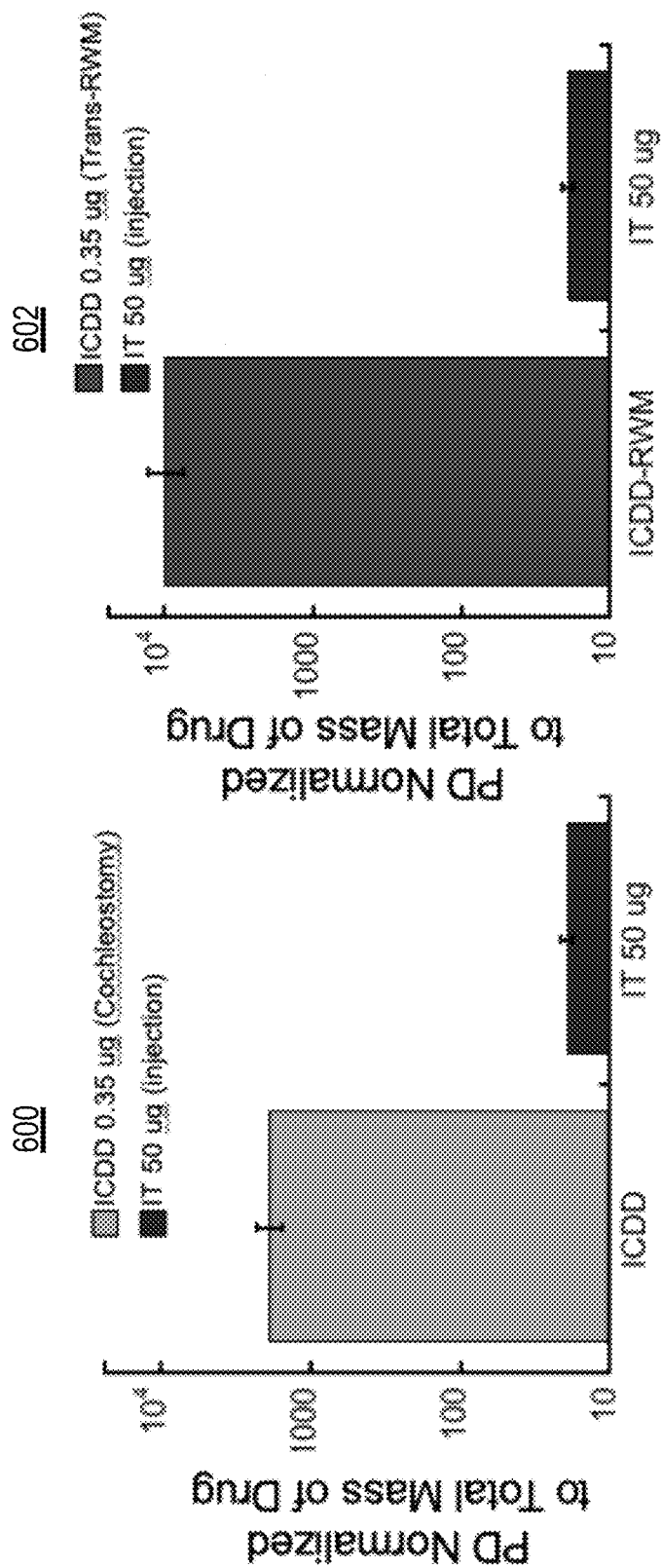

FIGS. 5 and 6 illustrate plots of PK (FIG. 5) and PD (FIG. 6) across different delivery methods. A drug was administered to the inner ear of guinea pigs. The guinea pigs were divided into three different groups. A drug was administered to the guinea pigs of the different groups via a different administration method. A first administration method included intratympanic injection (IT) of the drug. A second administration method included insertion of the cannula into the inner ear via a cochleostomy. A third administration method included insertion of the cannula into the inner ear via the round window membrane. The trans-round window membrane method of the third administration method is similar to the method described above in relation to FIG. 4.

For the cochleostomy and trans-round window membrane experiments, 0.35 µg of the drug was flowed into the inner ear. For the IT experiments, 50 µg of the drug was injected into the inner ear. Referring to FIG. 5, the plot 500 illustrates the PK, normalized to the total mass of the injected drug, for the cochleostomy injected drug versus the IT injected drug. The plot 502 illustrates the PK, normalized to the total mass of the injected drug, for the trans-round window membrane injected drug versus the IT injected drug. As illustrated in the plot 500 and the plot 502, the PK was the highest in the experiments where the drug was injected with a micropump in a method similar to that described above in relation to FIG. 4. Referring to FIG. 6, the plot 600 illustrates the PD, normalized to the total mass of the injected drug, for the cochleostomy injected drug versus the IT injected drug. The plot 602 illustrates the PD, normalized to the total mass of the injected drug, for the trans-round window membrane injected drug versus the IT injected drug. As illustrated in the plot 600 and the plot 602, the PD was the highest in the experiments where the drug was injected with a micropump in a method similar to that described above in relation to FIG. 4.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:
1. A system to deliver a fluid to the inner ear, comprising:
a micropump configured for implantation in a patient, the micropump comprising:
at least one first layer comprising a drug reservoir configured to store a compound, a fluid storage capacitor, and a plurality of channels between the drug reservoir and the fluid storage capacitor;
at least one second layer comprising a pump coupled with a reservoir inlet of the drug reservoir to pump the compound from the drug reservoir through a reservoir outlet of the drug reservoir through an outlet of the micropump; and a membrane separating the at least one first layer from the at least one second layer; and a cannula comprising:

a first end coupled with the outlet of the micropump; and a second end comprising a stopper configured to seat into a round window and enable a tip of the cannula to be inserted through a round window membrane and into a cochlea of the patient a predetermined distance.

2. The system of claim 1, wherein the pump is configured to inject a predetermined volume of the compound into the cochlea.

3. System of claim 2, wherein the pump is configured to withdraw at least a portion of the predetermined volume of a fluid from the cochlea after injecting the predetermined volume of the compound into the cochlea.

4. The system of claim 1, wherein the pump is configured to store the at least a portion of the predetermined volume of the fluid from the cochlea in the fluid storage capacitor.

5. The system of claim 1, wherein the tip of the cannula comprises a beveled tip configured to pierce the round window membrane.

6. The system of claim 1, further comprising a silicone-based glue to secure the cannula.

7. The system of claim 1, wherein the cannula comprises a first portion comprising polyetheretherketone and a second portion comprising polytetrafluoroethylene.

8. The system of claim 7, wherein the second portion comprises the tip of the cannula.

9. The system of claim 7, wherein the second portion is between about 2 cm and about 5 cm long.

10. The system of claim 7, wherein a stiffness of the second portion is greater than a stiffness of the first portion.

11. The system of claim 1, wherein the cannula has an inner diameter of between about 15 µm and about 150 µm.

12. The system of claim 1, wherein the cannula tip comprises a bevel between about 10 degrees and about 45 degrees.

13. The system of claim 1, wherein the drug reservoir is etched into the at least one first layer, and the fluid storage capacitor is a cylinder formed in the at least one first layer.

14. The system of claim 1, comprising a plurality of fluid storage capacitors in line with the plurality of channels and the drug reservoir, wherein the plurality of fluid storage capacitors comprises the fluid storage capacitor.

* * * * *